United States Patent [19]

Bachrach et al.

[11] 4,140,763
[45] Feb. 20, 1979

[54] VACCINE FOR FOOT AND MOUTH DISEASE

[75] Inventors: Howard L. Bachrach; Douglas M. Moore; Peter D. McKercher; Jerome Polatnick, all of Southold, N.Y.

[73] Assignee: The United States of America as represented by the Secretary of Agriculture, Washington, D.C.

[21] Appl. No.: 898,559

[22] Filed: Apr. 21, 1978

Related U.S. Application Data

[63] Continuation of Ser. No. 721,644, Sep. 8, 1976, abandoned.

[51] Int. Cl.$^2$ .............................................. A61K 39/26
[52] U.S. Cl. ...................................... 424/89; 195/1.4; 195/1.5
[58] Field of Search ........................................... 424/89

[56] References Cited

PUBLICATIONS

Vet. Bull. 46 #2965, #2969, Jun. 1976.
Vet. Bull. 45 #88, #1051, #3733, #5529, #5530 (1975).
Vet. Bull. 44 #584, #3067, #3681, #4925 (1974).
Vet. Bull. 43 #660, #662, #4890, #4893, #5495 (1973).
Vet. Bull. 42 #665, #668, #3307, #6833 (1972).

*Primary Examiner*—Shep K. Rose
*Attorney, Agent, or Firm*—M. Howard Silverstein; William E. Scott; David G. McConnell

[57] ABSTRACT

A vaccine comprised of a purified capsid protein of foot-and-mouth disease virus emulsified in an adjuvant was found to protect swine against the disease. The immunizing protein is the protein of the virus coat that is sensitive in situ to cleavage with trypsin. It is also the protein that migrates as $VP_3$ when isolated by the method of polyacrylamide gel separation used in this invention rather than migrating as $VP_1$, or $VP_2$ as it does when isolated by other methods.

6 Claims, No Drawings

VACCINE FOOT AND MOUTH DISEASE

This is a continuation, of application Ser. No. 721,644, filed Sept. 8, 1976, now abandoned.

BACKGROUND OF THE INVENTION

1. Field of the Invention

This invention relates to a vaccine for foot-and-mouth disease and more particularly to a vaccine which contains no intact nucleic acid molecules and in which the immunogenic substance is a purified subunit or capsid protein of a foot-and-mouth disease virus (FMDV).

2. Description of the Prior Art

FMDV is an acid-sensitive picornavirus that contains primarily four capsid proteins: $VP_1$, $VP_2$, $VP_3$, and $VP_4$, as well as a trace of precursor protein $VP_o$. The capsid proteins of FMDV collectively protect the viral ribonucleic acid core against environmental ribonuclease and other inactivating agents. However, the protein coat of FMDV is not as resistant to proteases as the coats of most enteroviruses. For example, in early experiments on the purification of FMDV, digestions with trypsin led to a marked reduction in infectivity without a corresponding loss in the number of virus particles.

This effect was later found to be caused by the tryptic cleavage of one of the capsid proteins, $VP_3$, into two peptides, $VP_{3a}$ and $VP_{3b}$, which remained in the capsid structure.

Although these capsid proteins of FMDV are known in the art and have been previously isolated (Biochem. Biophys. Res. Commun., 48, 1222, 1972; J. Gen. Virol., 4, 313, 1969; C. R. Acad. Sci. 276, 3399, 1973), no one, prior to this invention, has discovered that a capsid protein of FMDV could be used as the immunogenic portion of a vaccine to protect animals against exposure to infectious virus.

Since the vaccine of this invention contains no intact nucleic acid molecules, it eliminates the problem found in prior art vaccines of accidental infection because of insufficiently inactivated or modified nucleic acid. This invention also paves the way for synthesis of the immogenic protein or of that part of it needed to produce immunization, thereby eliminating the need for growing huge quantities of virus for vaccine, thus diminishing foci for introducing virus into animals in the field.

Practical vaccines in general use contain virus and cellular debris which can cause sensitization of animals receiving booster doses of vaccine and lead in some cases to the incapacitation or destruction of animals. Since the immunogenic protein of this invention is a pure protein, it reduces to an irreducible minimum the chance of sensitization of animals being vaccinated.

SUMMARY OF THE INVENTION

An object of this invention is to provide a vaccine for foot-and-mouth disease that is free of intact nucleic acid.

Another object of this invention is to provide a vaccine in which the immunogenic protein molecule is small enough to be synthesized, thus allowing for the preparation of a synthetic vaccine for foot-and-mouth disease.

According to this invention the above objects are accomplished by a vaccine for foot-and-mouth disease in which the immunogenic substance is a purified capsid protein of FMDV. The purified protein is that capsid protein of FMDV type $A_{12}$ strain 119 which is cleaved by trypsin and which migrates as $VP_3$ when isolated by disc polyacrylamide gel electrophoresis (PAGE) in 8M urea as described later. The capsid protein is emulsified with a suitable emulsifier or adjuvant such as Freund's incomplete adjuvant for use as a vaccine. Freund's incomplete adjuvant is prepared by mixing 9 parts Marcol 52 (a white mineral oil of national formulary grade with a viscosity of not more than 37 centistokes at 100° F. and a specific gravity range of 0.818 to 0.880 at 77° F.) and 1 part of Arlacel A (mannide monoleate, purest grade for use in human and veterinary adjuvant formulations) and filtering through a $0.45\mu$ filter.

DETAILED DESCRIPTION OF INVENTION

Foot-and-mouth disease virus type $A_{12}$ strain 119 was grown in rolling-bottle cultures of a baby hamster kidney cell line passage 21, clone 13, concentrated by precipitation with polyethylene glycol and purified by CsCl density-gradient centrifugation. As needed, purified virus ($10^{3.4}$ plaque-forming units (PFU/ml) was treated with 0.05% acetylethylenimine (AEI) at 25° C. for 72 hours. The treated virus retained its original complement-fixing activity but was innocuous for tissue cultures and animals. Five primary bovine kidney tissue cultures, each containing about 15 million cells, were inoculated with 300 $\mu$g of the AEI-treated virus in 0.1 ml. Two swine were each inoculated i.v. with 340 $\mu$g of the treated virus, and two steers each received the same dose intradermolingually divided equally among 20 sites. No signs of infectivity developed in any of the tissue cultures or animals.

Trypsinized virus, which contains the cleaved peptides $VP_{3a}$ and $VP_{3b}$ rather than $VP_3$, was prepared by incubating virus with L-(tosylamido 2-phenyl) ethyl cloromethyl ketone-treated trypsin (200:1 w/w) at 37° C. for 15 minutes. As needed, the trypsinized virus was separated from residual trypsin by centrifugation into a 10 to 50% sucrose density gradient in 0.2 M KCL-0.05 M potassium phosphate buffer at pH 7.5.

Virus proteins $VP_1$, $VP_2$, $VP_3$, and a mixture of peptides ($VP_{3a}$ and $VP_{3b}$ were isolated by disc PAGE; 8 M urea (Schwarz/mann. Orangeburg, New York, ultra pure) was present both in the hollow-cylindrical preparative gels (2.7 cm outside diameters × 1.1 cm inside diameter; stacking gel: 4%; separating gel: 10%) and sample preparation buffer which contained 0.06 M Tris-HCl, pH 7.1, 10% glycerine, 2% sodium dodecylsulfate (SDS), 5% $\beta$-mercaptoethanol (ME), 8 M urea, and phenol red. Sections containing the isolated proteins were cut from the gels, eluted electrophoretically into PAGE buffer (0.05 M Tris-0.4 M glycine, pH 8.1, 0.1% SDS) and, in some experiments, dialyzed against water containing 0.1% SDS and 0.01% ME adjusted to pH 9 with sodium carbonate. For certain experiments, SDS was quantitatively removed from $VP_3$ by the method of Weber and Kuter, J. Biol. Chem. 246, 4504, 1971. The method of disc PAGE has a high resolving power for FMDV proteins but causes the tryptic-sensitive capsid protein to migrate as $VP_3$ rather than as $VP_2$ in an earlier method (Biochem. Biophys. Res. Commun, supra) or as $VP_1$ in other laboratories (J. Gen. Virol. and C. R. Acad. Sci., supra).

Capsid protein $VP_3$ was also prepared from virus by anion-exchange column chromatography according to the method described in Biochem. Biophys. Res. Commun. 58, 624, 1974, except that quanternary amino ethyl (QAE) Sephadex A-25 was used. Approximately 7 mg of virus in 0.75 ml 0.2 M KCl-0.05 M potassium phosphate pH 7.5 were dialyzed against 0.014 M Tris-HCl, pH 8.6, containing 6 M urea (Tris-urea) buffer. The sample was made 8 M in urea, 1% in ME, heated at 100° C. for 2 minutes, and chromatographed with 0.014 M Tris-urea buffer at a flow rate of 20 ml/hr. The eluate was continuously scanned at 280 nm; 1 to 2 ml fractions were collected and selected for analysis of viral protein. After the appearance of $VP_3$ in fractions 4 to 8, the Tris-urea buffer was adjusted stepwise up to 0.6 M in NaCl, but no additional viral proteins could be identified up to 200 ml collected.

The purity, concentration, and recovery of the isolated proteins were established by disc PAGE on analytical 12.5% gels (0.6 cm × 10 cm). The bands were stained with Coomassie brillant blue and scanned at 600 nm in a recording spectrophotometer, and the areas under the peaks were converted to micrograms of protein with standard curves determined with the Folin phenol reagent.

Guinea pigs, in groups of five to 10, were vaccinated subcutaneously with individual virus proteins or a mixture of $VP_{3a}$ and $VP_{3b}$ emulsified in an equal volume of Freund's incomplete adjuvant and reinoculated at 28 or 30 days post vaccination (DPV) with the same protein. The vaccines contained 100 μg of protein in a total volume of 2 ml. Other guinea pigs inoculated originally with 100 μg of the mixture of $VP_{3a}$ and $VP_{3b}$ were reinoculated after 24 days with 0.5 μg of trypsinized virus. Guinea pigs also received single inoculations in oil adjuvant of 0.5 and 5.0 μg of AEI-treated virus or of trypsinized virus.

Swine, in groups of three or six, were vaccinated subcutaneously with virus protein or AEI-treated virus vaccines. Before inoculation, an equal volume of the appropriate antigen was emulsified in an equal volume of oil adjuvant. A group of three swine were inoculated on days 0 and 28 with $VP_3$ from AEI-treated virus. The first swine received 100 μg doses; the second received 500 μg doses; and the third, 600 μg doses. A fourth swine (nonvaccinated) was housed with the three inoculated swine. A second group was inoculated on days 0, 28, and 60 with proteins from virus not treated with AEI; two swine received 100 μg doses of $VP_3$; two received 100 μg doses each of $VP_1$, $VP_2$, and $VP_3$ administered at separate inoculation sites; and two received a mixture containing 100 μg each of $VP_1$ $VP_2$, and $VP_3$. Two additional swine in the second group received adjuvant only. Six swine in a third group were vaccinated with 10 μg doses of AEI treated virus in a total volume of 2 ml; three of the six were revaccinated at 28 DPV.

Another group of 10 swine were vaccinated on days 0 and 28 with 100 μg of $VP_3$ emulsified with Freund's incomplete adjuvant. The $VP_3$ was isolated from virus that had not been treated with AEI.

Although other well known adjuvants and emulsifiers can be used to make the vaccine of this invention, we used Freund's incomplete adjuvant because it was convenient and readily available.

Blood samples for the preparation of serums were collected after appropriate intervals, up to 50 DPV for guinea pigs and 82 DPV for swine. Serums were also prepared from swine blood taken 14 days post-challenge (DPC). An Ouchterlony procedure (Virology 30, 528, 1966) in 0.75% agarose gels was used to test the serums for precipitating antibody against purified type $A_{12}$, $O_1$, and $C_3$ viruses as well as against type $A_{12}$ trypsinized virus and a 12S subunit degradation product of virus which contains only $VP_1$, $VP_2$, and $VP_3$. Neutralizing antibody titers of serums were determined ad 50% protective doses per milliliter ($PD_{50}$) in suckling mice.

The immunity of the swine was challenged at 56 DPV and at 82 DPV by contact exposure to infected swine as described in Appl. Microbiol. 20, 770, 1970. Two non-vaccinated swine were each inoculated in the footpads of one foot with 40,000 $ID_{50}$ of homologous type $A_{12}$ virus, and two additional nonvaccinated swine were used to monitor virus transmission. All four swine developed generalized infections of foot-and-mouth disease (vesicular lesions on snout and all four feet) within 72 hours, providing a severe contact exposure for the vaccinated swine. In experiments with the capsid protein vaccines, the nonvaccinated swine which had been housed with the vaccinated swine before challenge also developed a generalized infection during exposure.

Type $A_{12}$ capsid proteins $VP_1$, $VP_2$, $VP_3$, the mixture of $VP_{3a}$ and $VP_{3b}$, and trypsinized virus were examined by analytical disc PAGE. No contamination of any of the virus protein preparations was detected by scanning the gels at 600 nm. Before trypsinized virus was used in vaccine and precipitin tests, the residual trypsin was removed by centrifugation in a 10 to 50% sucrose density gradient.

Antibody levels of serums from guinea pigs vaccinated twice with purified capsid proteins and AEI-treated type $A_{12}$FMDV at days 0 and 30 were determined. No virus precipitating or neutralizing activities were detected in serums from guinea pigs which received $VP_1$ or $VP_2$. However, both activities were detected in many serums of guinea pigs inoculated with various $VP_3$ preparations ($VP_3$ containing tightly bound SDS, SDS-free $VP_3$, $VP_3$ prepared by QAE Sephadex chromatography, and $VP_3$ prepared from AEI-treated virus) and in all serums of guinea pigs vaccinated with AEI-treated virus. The highest neutralizing antibody response produced by capsid protein vaccine was 2.8 log $PD_{50}$ observed in one guinea pig following two doses of $VP_3$ isolated by QAE Sephodex chromatography, whereas viral precipitating antibody was produced more regularly with $VP_3$ from AEI-inactivated virus. Virus vaccine induced consistently higher antibody responses in guinea pigs than of the various $VP_3$ preparations.

Antibody responses of guinea pigs vaccinated with AEI-treated FMDV, trypsinized AEI-treated virus, and a mixture of $VP_{3a}$ and $VP_{3b}$ were also determined. The 0.5 μg doses of the virus or trypsinized virus produced no virus precipitating antibody detectable in agarose gels and only marginally positive neutralizing antibody; however, 5 μg doses of either antigen elicited strong viral precipitating and neutralizing antibody responses. A 100 μg dose of the $VP_{3a}$ $VP_{3b}$ mixture followed at 28 DPV by a second dose produced no detectable antiviral antibodies; however, when the second inoculation was a marginally effective 0.5 μg dose of trypsinized virus, viral precipitating (4 of 4 serums positive) and neutralizing (2.3 log $PD_{50}$) antibody responses resulted which were about equal to those produced by a single 5 μg dose of virus or trypsinized virus. Although the mixture of $VP_{3a}$ and $VP_{3b}$ did not induce detectable antibody levels, it apparently sensitized guinea pigs to an immunogenic determinant (presumably in $VP_{3a}$ or $VP_{3b}$) of the trypsinized virus.

Neutralizing antibody responses to initial inoculations of swine with $VP_3$ from AEI-treated virus were lower than 2.0 log $PD_{50}$, but reinoculations at 28 DPV quickly increased antibody levels to 3.0 log $PD_{50}$ or higher for the 100 and 500 µg doses and to about 2.0 log $PD_{50}$ for the 600 µg dose. Serums from these swine taken 14 DPC contained about 3.7 log $PD_{50}$ of neutralizing antibody regardless of the differences in their pre-challenge levels.

Neutralizing antibody responses of swine inoculated with $VP_3$, with $VP_1$, $VP_2$ and $VP_3$ administered singly at separate sites or with $VP_1$, $VP_2$ and $VP_3$ administered as a mixture at a single site, all from virus not treated with AEI, were initially weak, lower than 1.0 log $PD_{50}$. The responses to $VP_3$ and to $VP_1$, $VP_2$ and $VP_3$ administered separately were boosted by revaccination at 28 days to about 2.0 log $PD_{50}$. The response of swine to the mixture of $VP_1$, $VP_2$ and $VP_3$ remained at a very low level even after revaccination. Second revaccinations at 60 days boosted the responses to about 2.5 log $PD_{50}$ in swine which received $VP_3$ alone or $VP_1$, $VP_2$ and $VP_3$ administered separately, but to only 1.5 log $PD_{50}$ or less in swine which received the mixture of $VP_1$, $VP_2$, and $VP_3$. The 14 DPC serums from these swine contained 2.1 log $PD_{50}$($VP_3$ alone, 2.2 log $PD_{50}$($VP_1$, $VP_2$, $VP_3$ individually administered), and 3.6 log $PD_{50}$($VP_1$, $VP_2$, $VP_3$ administered as a mixture.

A peak neutralizing antibody titer of about 3.4 log $PD_{50}$ was found in swine which received a single 10 µg dose of AEI-treated virus. Revaccination of three swine at 28 DPV boosted their average response to about 4.0 log $PD_{50}$. The 14 DPC serum titers of these swine were about 4.2 log $PD_{50}$.

The immune responses of swine inoculated with purified capsid proteins and with AEI-treated virus are shown in Table 1. The swine were challenged 82 DPV by exposure to infected swine as described previously and in footnote b of Table 1. Although the three swine inoculated with $VP_3$ from AEI-treated virus were not fully protected, they showed fewer and less severe clinical signs of disease than did the five nonvaccinated controls. Two swine were protected against snout lesions and partially protected against foot involvement. The third swine, which developed snout and foot lesions, also had the lowest prechallenge neutralizing antibody level of this group of animals as noted above (about 2.0 log $PD_{50}$ after reinoculation at 28 DPV).

Swine inoculated with $VP_3$ isolated from virus not treated with AEI did not develop fevers, lesions, or any other signs of illness when exposed to infected swine. Swine which had received separate inoculations of $VP_1$, $VP_2$, and $VP_3$ at different sites were also completely protected against challenge. One of the two swine which had been inoculated with the mixture of $VP_1$, $VP_2$, and $VP_3$ was resistant to challenge. The other swine, having had the lowest of all prechallenge neutralizing antibody responses, developed a small localized foot lesion late in the challenge period (9 DPC).

In contrast to the 100 µg doses of $VP_3$ used to inoculate swine, a single vaccination with a 10 µg dose of AEI-treated virus was sufficient to protect swine against exposure to infected swine.

The ten swine (not shown in Table I) that were vaccinated on days 0 and 28 with 100 µg of $VP_3$ emulsified in Freund's incomplete adjuvant were challenged on day 56 by exposure to infected swine. All ten were protected against generalized foot-and-mouth disease. Eight showed no visible lesions and two each developed only a rapidly healing localized foot lesion late in the challenge period (12 DPC). By contrast, all 13 nonvaccinated control swine developed generalized foot-and-mouth disease with lesions on the snout and all four feet.

The vaccine of this invention has a number of advantages over vaccines currently in use. It is free of intact nucleic acid thus eliminating the possibility of inducing clinical disease which occasionally occurs from vaccination with presently available inactivated or modified live virus vaccines. The immunogenic protein molecule of the vaccine of this invention is small enough to be synthesized; consequently, this invention is an important step leading to the development of a synthetic vaccine for foot-and-mouth disease and other diseases of a similar nature. The vaccine of this invention also reduces the possibility of sensitizing vaccinated animals with revaccinations because it contains a single pure protein rather than a mixture of proteins.

Although, for the purposes of this invention, only type A foot-and-mouth disease virus has been discussed and demonstrated, the invention is applicable to the other six types of the disease, namely, O, C, $SAT_1$, $SAT_2$, $SAT_3$, and Asia. A vaccine for immunizing animals against these types of FMDV may be prepared by isolating the immunogenic protein molecule of each type and combining it with a suitable adjuvant. In addition, since all picornaviruses such as poliovirus, human rhino virus, cattle enteoviruses, and swine vesicular disease virus, have essentially the same architectural structure as FMDV, that is, four major coat proteins and 2.6 million dalton ribonucleic acid core, there appears to be no reason why vaccines immunogenic against all picornaviruses cannot be made in the same way that the vaccine of this invention is made.

TABLE 1

Immune response of swine vaccinated with purified capsid proteins and AEI-treated type $A_{12}$ FMDV

| Vaccinations[a] | | | Response to Challenge at 82 DPV[b] | | | |
|---|---|---|---|---|---|---|
| | Dose | | | | Foot Involvement | |
| Antigen | µg | No. | No. of swine | Snout lesions[c] | No. | Lesions[c] |
| $VP_3$ | 100 | 2 | 1 | None | 2 | + |
| $VP_3$ | 500 | 2 | 1 | None | 2 | ++ |
| $VP_3$ | 600 | 2 | 1 | + | 4 | ++++ |
| None | | | 5 | ++++ | 4 | ++++ |
| $VP_3$ | 100 | 3 | 2 | None | None | None |
| $VP_1$, $VP_2$, $VP_3$ | 100 ea | 3 | 2 | None | None | None |
| $VP_1$-$VP_2$-$VP_3$ | 100 ea | 3 | 2 | None | 1[d] | +[d] |
| None | | | 6 | ++++ | 4 | ++++ |
| Virus | 10 | 1 | 3 | None | None | None |
| Virus | 10 | 2 | 3 | None | None | None |

TABLE 1-continued

| | Immune response of swine vaccinated with purified capsid proteins and AEI-treated type $A_{12}$ FMDV | | | | | |
|---|---|---|---|---|---|---|
| | Vaccinations[a] | | | Response to Challenge at 82 DPV[b] | | |
| | Dose | | | | Foot Involvement | |
| Antigen | μg | No. | No. of swine | Snout lesions[c] | No. | Lesions[c] |
| None | | | 4 | ++++ | 4 | ++++ |

[a]The first three $VP_3$ preparations were prepared from AEI-treated virus; all other capsid proteins were from nontreated virus; $VP_1$, $VP_2$, $VP_3$ were individually administered subcutaneously at separate sites; $VP_1$-$VP_2$-$VP_3$ is a mixture of the three proteins administered at a single site. Dosage is in micrograms per vaccination. First, second, and third vaccinations were administered on days 0, 28, and 60.
[b]Challenge: two of the nonvaccinates were inoculated with 40,000 mouse $ID_{50}$ of $A_{12}$ virus and two served as contact nonvaccinates. The additional nonvaccinates (one sentinel swine in the first group and two in the second) had been continuously housed with the capsid protein vaccinates even before challenge. All of these swine developed lesions on their four feet and snouts.
[c]Lesions: +, minute and healed over; ++, small open but healing over; ++++, larger and open.
[d]This foot lesion was in only one of the two animals, and it did not appear until 9 DPC.

We claim:

1. An immunological composition comprising a purified capsid protein, $VP_3$, of FMDV emulsified with a suitable adjuvant.

2. A vaccine effective against FMDV comprising a purified capsid protein of FMDV Type $A_{12}$ strain 119 emulsified with a suitable adjuvant, said purified protein being that capsid protein which is cleaved into two peptides by trypsin and which migrates as $VP_3$ when isolated by disc polyacrylamide gel electrophoresis in 8 M urea.

3. The vaccine of claim 2 in which the adjuvant is Freund's incomplete adjuvant.

4. A vaccination method for protecting an animal against foot-and-mouth disease comprising inoculating said animal with an effective immunizing amount of a purified capsid protein of FMDV emulsified with a suitable adjuvant, and, about 28 days after the initial inoculation, reinoculating the animal with another effective immunizing amount of the purified capsid protein of FMDV emulsified with a suitable adjuvant, said protein being that capsid protein which is cleaved into two peptides by trypsin and which migrates as $VP_3$ when isolated by disc polyacrylamide gel electrophoresis in 8 M urea.

5. A vaccination method for protecting an animal against foot-and-mouth disease comprising inoculating the animal with 100 μg of a purified capsid protein of FMDV Type $A_{12}$ strain 119 emulsified with a suitable adjuvant and reinoculating the animal about 28 days after the initial inoculation with another 100 μg of said purified capsid protein emulsified with a suitable adjuvant, said purified protein being that capsid protein of FMDV which is cleaved into two peptides by trypsin and which migrates as $VP_3$ when isolated by disc polyacrylamide gel electrophoresis in 8 M urea.

6. The vaccination method of claim 5 in which the adjuvant is Freund's incomplete adjuvant.

* * * * *